United States Patent

Naessens

(10) Patent No.: US 6,596,295 B2
(45) Date of Patent: Jul. 22, 2003

(54) AQUEOUS SOLUTION FOR TREATING DEGENERATIVE OR AUTOIMMUNE DISEASES AND/OR AS AN IMMUNOMODULATORY AGENT

(76) Inventor: Gaston Naessens, 5260, rue mills, Rock Forest, Quebec (CA), J1N 3B6

( * ) Notice: Subject to any disclaimer, the term of this patent is extended or adjusted under 35 U.S.C. 154(b) by 0 days.

(21) Appl. No.: 10/199,990

(22) Filed: Jul. 19, 2002

Related U.S. Application Data

(63) Continuation of application No. PCT/CA01/00188, filed on Jan. 31, 2001.

(30) Foreign Application Priority Data

Feb. 3, 2000 (CA) ............................................ 2297998

(51) Int. Cl.[7] .......................... A61F 13/00; A61K 9/00; A61K 33/02
(52) U.S. Cl. ....................... 424/422; 424/434; 424/400; 424/719; 424/721
(58) Field of Search ................................ 424/422, 434, 424/400, 719, 721

(56) References Cited

FOREIGN PATENT DOCUMENTS

| GB | 385 148 A | 12/1932 | |
| WO | 97 05780 A | 2/1997 | .......... A01N/27/00 |

OTHER PUBLICATIONS

XP002167940, vol. 29, No. 3, 1896, pp. 2807–2808.

*Primary Examiner*—Thurman K. Page
*Assistant Examiner*—Robert M. Joynes
(74) *Attorney, Agent, or Firm*—Darby & Darby

(57) ABSTRACT

The invention concerns an aqueous solution capable of being injected by perinodular delivery or inhaled for use in the treatment of degenerative or autoimmune diseases or as immunomodulatory agent. Said solution is prepared by reacting camphor on ammonium hydroxide. The resulting product is then suspended in a saline solution. Said preparation having a basic pH is then neutralized with nitric acid. The resulting aqueous solution has pharmacological properties since it is an analogue of human cytokines, which makes it useful for treating degenerative or autoimmune diseases and/or as an immunomodulatory agent.

6 Claims, 1 Drawing Sheet

Figure 1:
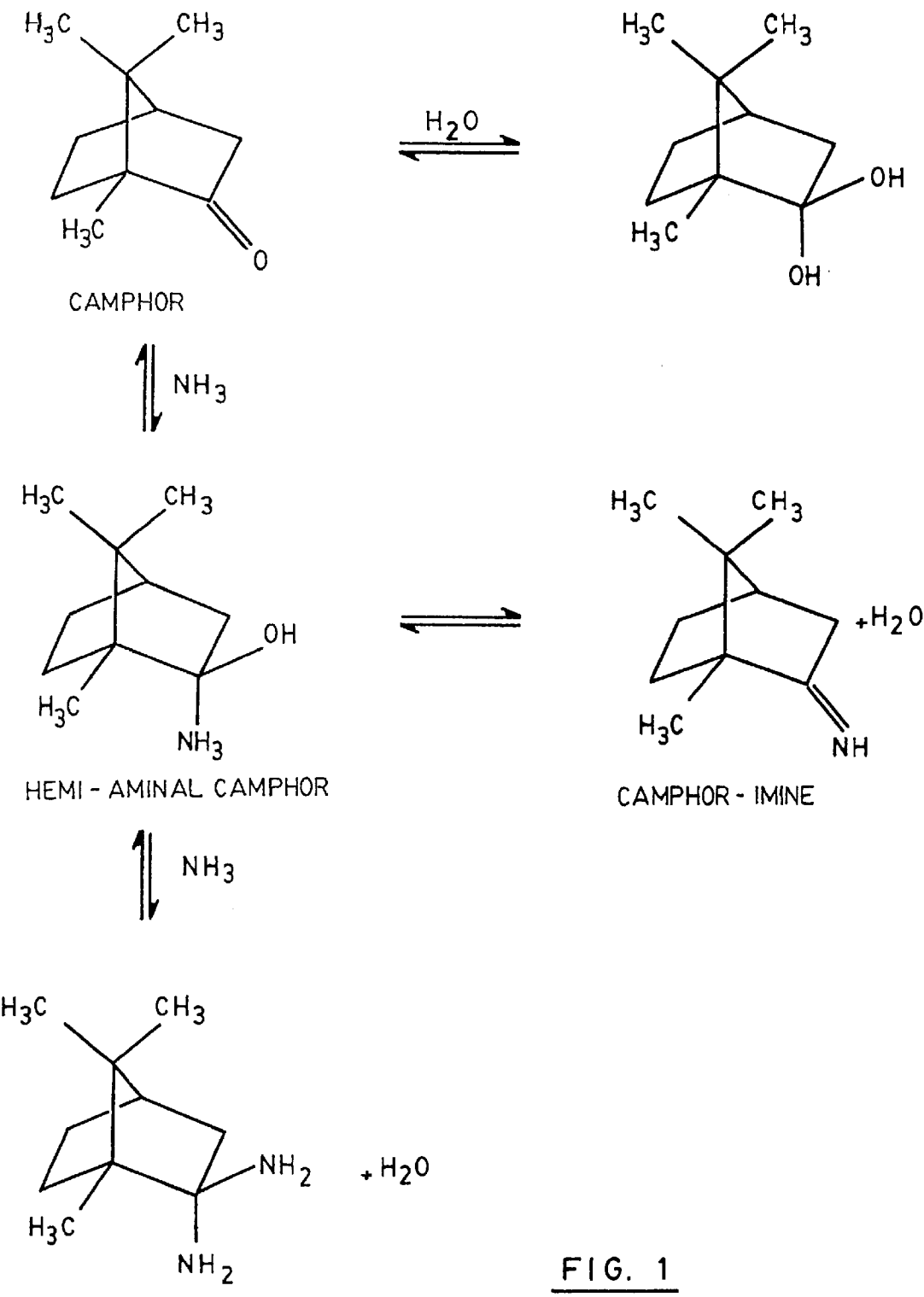

AQUEOUS SOLUTION FOR TREATING DEGENERATIVE OR AUTOIMMUNE DISEASES AND/OR AS AN IMMUNOMODULATORY AGENT

This application is a continuation of PCT/CA01/00108 filed Jan. 31, 2001.

The present invention relates to an aqueous solution that is administrable by perinodular injection or by inhalation and is usable for treating degenerative or autoimmune diseases and/or as an immunomodulatory agent.

The invention also relative to a method for preparing this solution.

This method is characterized in that:

in a first step, camphor is reacted with ammonium hydroxide;

in a second step, the product obtained in the first step is suspended in an aqueous solution of sodium chloride; and in a third step, the pH of the liquid suspension obtained in the second step is neutralized with nitric acid to obtain the desired aqueous solution.

The aqueous solution according to the invention as obtained by the method described above, has been thoroughly tested and has proven to have pharmacological properties which make it efficient for the treatment of degenerative or autoimmune diseases and/or as an immunomodulatory agent.

Thus, it has been noticed that it mimicks human cytokines. Thus, it acts on monocytes to transform them into macrophages which, in turn, secrete two proinflammatory cytokines: interleukin 1 beta, 6, 8α and a tumor necrosis factor TNF alpha. Depending on the mimicked cytokine family, monocytes are transformed into macrophages or block molecules which paralyse the immune system. In both cases, a stimulation of the immune system and an increase in the tumor necrosis factor, which is also classified among immunostimulating factors, occur. This factor is also known for the role it plays in host resistance against viral infections or others, and in tumor development.

Based on testings performed on animals, the solution according to the invention would be applicable in human therapeutics using 0.075 ml per pound of body weight for 21 days, that is to say a total of 10.5 ml per series, which corresponds to 0.5 ml per day for a person weighing 140 pounds. Administration can be done by perinodular injection or by inhalation with an ultrasonic nebulizer.

For a person of 140 to 190 pounds, the first series should be applied in a progressive way according to the following schedule:

| | |
|---|---|
| 1st day | 0.1 ml injection |
| 2nd day | 0.2 ml injection |
| 3rd day | 0.3 ml injection |
| 4th day | 0.4 ml injection |
| 5th day | 0.5 ml injection |

All the other injections should comprise the same volume (0.5 ml) of injected product.

The following series will use 0.5 ml at each injection for 21 days.

Cycles can be repeated if needed with an interruption of 2 days between each cycle.

The structure of the active principle present within the aqueous solution according to the invention has not been established with precision yet. As it stands out on the reaction diagram identified as FIG. 1 in appendix, camphor reacts in a reversible way with ammoniac to produce a hemiaminal derivative. This hemiaminal derivative of camphor is itself prone to a number of possible reversible conversions in the presence of ammoniac and water, and has been impossible to identify by infrared spectrophotometry yet. However, the Applicant however thinks that it is the chloride of this hemiaminal derivative of camphor obtained in the second step of neutralization which is probably the active principle of the aqueous solution insofar as the structure of this derivative could effectively mimick the structure of β family cytokines which are known to act on monocytes and stimulate the production of IL-1 beta, 6, 8 and TNF alpha. The complete chemical name of the chloride derivative is the trimethyl-1,7,7 amino-2 hydroxy-2-bicyclo [1,2,2] heptane chloride.

The invention will be better understood upon reading what will follow in a practical example of synthesis and the detailed description of assays performed up to now by the Applicant.

EXAMPLE

In a container sealed hermetically, 108 mg of camphor ($C_{10}H_{16}O$) is added to 0.9 ml of ethyl alcohol ($C_2H_5O$), until complete dissolution. Then, the alcoholic solution so obtained is added to 5.2 ml of ammonium hydroxide ($NH_4OH$). The obtained mixture is shaken.

In another erlenmeyer, 0.9 g of sodium chloride (NaCl) is dissolved in 79 ml of sterile, non pyrogenic water. The content of this other erlenmeyer is added to the mixture previously prepared. The new mixture obtained is vigorously shaken.

The so prepared aqueous solution presents a fluffy precipitate and supernatant. After three days at room temperature and daily shaking, the precipitate is completely dissolved.

The aqueous solution is in the form of a clear liquid, with an ammoniacal smell and an alkaline flavour, the pH of which is 10.4. Then, the pH is adjusted to 7 by introducing 14.9 ml of nitric acid $(HNO_3)N_6$.

The final solution obtained is then filtered through a millipore filter of 0.2 micron.

It is obvious that the basic chemical products used and previously mentioned comply with the U.S.P. standards and are manipulated in conditions of total asepsis.

Biological Properties

The biological properties which were obtained with the solution prepared as described in the preceding example, are the following:

1) It acts on monocytes in vitro.
2) It transforms monocytes into mature macrophages in vitro.
3) In vitro again, transformed macrophages are stimulated to secrete proinflammatory cytokines.
   (a) Interleukin-1 beta (IL-1 beta) known to exert a large variety of effects on differentiation and function of cells involved in inflammatory processes and immune responses; and
   (b) IL-6, 8 alpha and tumor necrosis factor (TNF alpha), also classified as an immunostimulatory agent and known to play a role in host resistance against infections and tumor development.

It is known that the cellular immune response is controlled and modulated by a family of relatively small molecules called <<(cytokines)>> which are small protein hormones playing a role in numerous normal cell functions. Their functions encompass anti-tumor, anti-viral and anti-bacterial activities and they induce immune cell growth, differentiation, activation, chemotactism, adhesion and immunosuppression.

This family of immunomodulators has recently been discovered. More than 70 different molecules have been identified but it seems that the family comprises more than 200 members. In other words, to date, cytokines are only partially known and characterized.

Known cytokines have been divided into two groups, alpha and beta, based on their structure. Alpha cytokines include interleukins, interferons, and other growth factors which control immune cell proliferation. Beta cytokines include MIP (Macrophage Inflammatory Proteins), MCP (Monocyte Chemoattractant Proteins), RANTES, and other proteins which attract immune cells toward a site of infection or a tumor and, in doing so, strengthen the activity of the immune system. It seems that each cytokine molecule is very specific and only targets a small subpopulation of lymphocytes. In addition, cytokine fragments as small as 3 to 7 amino acids can bind to lymphocytes and partially mimick or block the activity of a complete cytokine molecule.

It is also known that the last three amino acids at the C-terminal end of beta cytokines are nitrogen-oxygen which bear a positive charge. It is thus possible that the aqueous solution according to the invention could exert a stimulatory effect to secrete cytokines since, as a result of its preparation, it may contain a small amount of nitrogen-oxygen molecules which look like and mimick the three amino acid-sequence of the beta cytokine family. Depending on the required cytokine activity, the solution according to the invention can either activate the transformation of monocytes into active macrophages or block the action of other molecules which paralyse the immune system. In either case, the result could be reinforcement of the immune system and the natural defenses to increase tumor cell destruction.

Results of the Assays Carried Out

Various assays and tests described thereafter were carried out with vials filled with the aqueous solution prepared according to the example given hereinabove.

1) Control Tests of the Solution

The aqueous solution prepared according to the invention was tested. In practice, it should be limpid, clear and volatile, and leave a dry extract of 63 mg per ml.

2) Sterility Assays

Ten randomly selected vials were incubated at 37 degrees for 48 hours. Then, each vial content was seeded as follows:
   a) 1 ml of solution respectively in two tubes of 60 ml containing thioglycolate medium (Difco) and a tube of 60 ml containing Sabouraud liquid medium (Difco).
   b) 0.25 ml of solution respectively in two tubes of 60 ml containing thioglycolate medium (Difco) and a tube of 60 ml containing Sabouraud liquid medium (Difco).
   c) A thioglycolate tube of group A and a thioglycolate tube of group B were incubated at 35 degrees for 10 days, all the other tubes being kept for 10 days at room temperature (about 20 degrees).

All seeded tubes were maintained sterile.

3) Toxicity Assays

Pharmacological assays performed on healthy animals showed an absence of toxicity, even at very high doses.

Then, one was able to intravenously inject 1 ml of product to a 9-pound rabbit, without being in a position to observe an unfavourable reaction. In the same way, one was able to inject 0.2 ml of product per pound of body weight to cats and 0.3 ml of product per pound of body weight to dogs without observing unfavourable reactions.

By lymphatic delivery, one was able to inject to cats of 10 to 12 pounds up to twice the total dose prescribed in human therapeutics, for a body weight of 140 to 190 pounds, without observing unfavourable reactions.

4) Therapeutic Assays

The therapeutic activity of the product was observed for almost three years in 26 cats and 20 dogs suffering from various degenerative pathologies as well as viral and bacterial infections.

Single injected doses varied by one twentieth up to the total dose proposed above in human therapeutics.

The therapeutic activity of the product was observable in all cases right from the second day of treatment. This activity presented itself either by regression of tumor or lymph node masses, or by resumption to vital functions and return to a satisfying general state after infectious diseases.

Optimal results were recorded with a posology of 0.075 ml per pound of body weight, for a 21-day cycle, which has permitted to establish the previously mentioned posology applicable to human therapeutics.

5) Pharmacological Assays

As previously indicated, the aqueous solution according to the invention acts on neoplastic cells and prevents them from secreting a substance which drives leucocytes and other phagocytic elements of the organism into a state of negative chemotactism.

Suppression of this secretion then allows the immune system to consider the neoplastic formation as a foreign body and destroy it. Animal testing showed that elimination of lysed tumor masses occurs through emunctories. Cancer cells thus evacuated present a nuclear disruption making any mitosis impossible. These evacuated cells are surrounded by an enormous amount and variety of very active leucocytes.

Animal testing also showed that hematological constants in treated animals reached standard levels right from the first week of treatment.

The aqueous solution according to the invention can be used as such, preferably by lymphatic delivery.

From a practical point of view, it is worth noting that this solution can not be exposed to germicidal tube rays (a 2537 angstrom-ray for example).

What is claimed is:

1. A method for preparing an aqueous solution that is administrable by perinodular injection or by inhalation and is usable for treating degenerative or autoimmune diseases and/or as an immunomodulatory agent, characterized in that:
   in a first step, camphor is reacted with ammonium hydroxide;
   in a second step, the product obtained in the first step is suspended in an aqueous solution of sodium chloride; and
   in a third step, the pH of the liquid suspension obtained in the second step is neutralized with nitric acid in order to obtain the desired aqueous solution.

2. The method according to claim 1, characterized in that in the first step, camphor is reacted with ammonium hydroxide in an alcoholic medium.

3. The method according to claim 2, characterized in that:
   in the first step, 108 mg of camphor in 0.9 ml of ethyl alcohol is reacted with 5.2 ml of ammonium hydroxide;
   in the second step, the product obtained in the first step is fully dissolved in a solution comprising 79 ml of water and 0.9 g of sodium chloride; and in the third step, the pH is adjusted to 7 by adding 14.9 ml of nitric acid with a concentration of N/6.

4. The method according to claim 1, wherein the aqueous solution obtained in the third step is filtered through a millipore filter.

5. An aqueous solution administrable by perinodular injection or by inhalation for treating degenerative or autoimmune disease and/or as an immunomodulatory agent, whenever prepared by the method according to claim 1.

6. The method according to claim 3, wherein the aqueous solution obtained in the third step is filtered through a millipore filter.

* * * * *